(12) United States Patent
Quijano et al.

(10) Patent No.: US 7,530,995 B2
(45) Date of Patent: May 12, 2009

(54) DEVICE FOR REDUCTION OF PRESSURE EFFECTS OF CARDIAC TRICUSPID VALVE REGURGITATION

(75) Inventors: Rodolfo C. Quijano, Laguna Hills, CA (US); Patrick M. McCarthy, Hunting Valley, OH (US)

(73) Assignee: 3F Therapeutics, Inc., Lake Forest, CA (US)

( * ) Notice: Subject to any disclaimer, the term of this patent is extended or adjusted under 35 U.S.C. 154(b) by 595 days.

(21) Appl. No.: 10/418,677

(22) Filed: Apr. 17, 2003

(65) Prior Publication Data

US 2004/0210306 A1    Oct. 21, 2004

(51) Int. Cl.
  A61F 2/06   (2006.01)
  A61M 29/00   (2006.01)
(52) U.S. Cl. .................................. 623/1.24
(58) Field of Classification Search .............. 623/1.24, 623/1.26, 900, 904
  See application file for complete search history.

(56) References Cited

U.S. PATENT DOCUMENTS

| | | | |
|---|---|---|---|
| 4,477,930 A * | 10/1984 | Totten et al. .............. | 623/2.15 |
| 4,806,595 A | 2/1989 | Noishiki et al. | |
| 5,607,465 A | 3/1997 | Camilli | |
| 5,824,061 A | 10/1998 | Quijano et al. | |
| 5,855,601 A | 1/1999 | Bessler et al. | |
| 5,928,181 A | 7/1999 | Coleman et al. | |
| 5,997,573 A | 12/1999 | Quijano et al. | |
| 6,299,637 B1 | 10/2001 | Shaolian et al. | |
| 6,319,278 B1 * | 11/2001 | Quinn ..................... | 623/1.13 |
| 6,319,281 B1 | 11/2001 | Patel | |
| 6,383,193 B1 | 5/2002 | Cathcart et al. | |
| 6,451,025 B1 | 9/2002 | Jervis | |
| 6,503,272 B2 | 1/2003 | Duerig et al. | |
| 6,508,833 B2 * | 1/2003 | Pavcnik et al. ............. | 623/1.15 |
| 7,159,592 B1 * | 1/2007 | Makower et al. ............ | 128/898 |
| 2001/0011187 A1 | 8/2001 | Pavcnik et al. | |

FOREIGN PATENT DOCUMENTS

WO    WO9808456 A1    5/1998

* cited by examiner

Primary Examiner—Vy Q. Bui
(74) Attorney, Agent, or Firm—Barbara A. Wrigley; Oppenheimer Wolff & Donnelly, LLP

(57) ABSTRACT

A method of protecting an upper and a lower body of a patient from high venous pressures comprising: providing an elongate valve stent, wherein the stent comprises a first stent member with a first tissue valve secured to a first support structure being disposed at a first end of the stent and a second stent member with a second tissue valve secured to a second support structure being disposed at an opposite second end of the stent, wherein both support structures are collapsibly expandable, the second end being connected to the first end with at least one elongate connecting member; passing the elongate valve stent through a blood vessel with the first and second support structures in a collapsed position; and securing the first support structure to an inferior vena cava and the second support structure to a superior vena cava with both support structures in an expanded shape.

26 Claims, 6 Drawing Sheets

DEVICE FOR REDUCTION OF PRESSURE EFFECTS OF CARDIAC TRICUSPID VALVE REGURGITATION

FIELD OF THE INVENTION

The present invention relates generally to stented venous valves and, more particularly, to stented valve bioprostheses and methods for reduction of pressure effects of cardiac tricuspid valve regurgitation and methods thereof.

BACKGROUND OF THE INVENTION

Among the quadruped heart valves in a human body, the tricuspid valve separates the right atrium (upper chamber) from the right ventricle (lower chamber), and channels the venous blood return to the heart on its way to the lungs. When the venous blood is impelled to the lung arteries, this tricuspid valve closes to block the blood return from backflowing to the atrium and thus provides efficiency to the ejection of blood from the right ventricle that directs the flow towards the lung. In instances where the tricuspid valve is unable to close properly, the pumping pressure of the ventricle can be transmitted in reverse to the atrium and subsequently to the vena cavae. Typically, the superior vena cava functions to bring blood to the heart from the head and the inferior vena cava functions to bring blood to the heart from the liver and other parts of the body (kidneys, gut, legs) that are located below the heart. This pressure can have deleterious effects on the work of the heart and circulatory system. The device herein described provides means of reduction or total nullification of the effects of pressure on the channels of venous return to the heart.

The tricuspid heart valve has an area close to 10 square centimeters, and a circumference approaching 12 centimeters. As the name implies it has three cusps or leaflets that separate to open the valve and allow the venous return from the body to the heart to enter the pumping chamber or right ventricle that redirects the flow towards the lung where venous blood is oxygenated and transformed into arterial blood to supply all tissues of the body. During the pumping action, the tricuspid valve closes to impede retrograde flow into the right atrium.

Acquired disease of the tricuspid valve is much less common than that of the other valves of the heart; this is a reflection of the lower pressures that are experienced by the right chambers of the heart, and thus, the valves of the right side of the heart function generally under less stresses than its left side counterparts. Disease can affect the tricuspid valve mostly in two forms, 1) as tricuspid valve stenosis, a restriction of the opening of the valve, most likely of rheumatic origin, and 2) as tricuspid valve regurgitation or incompetence, generally due to any disease process that causes alterations in the tricuspid valve apparatus that consists of: leaflets, chords, tendinous material that join the leaflet to the muscle of the right-side of the heart, or the annulus (the ring of tissue where the leaflets join the atrium). In the latter, the valve is unable to close completely thus allowing retrograde flow or regurgitation from the ventricle into the atrium.

A small degree of tricuspid regurgitation is found in normal hearts and the prevalence increases with age. Physiologically, the regurgitation is seen as a jet whose velocity is proportional to the pressure differential between the right ventricle and the right atrium. Tricuspid regurgitation (TR) alone may be well tolerated. However, patients suffering from severe TR are troubled with swelling of the legs, pulsations of the jugular vein pulse at the neck due to reverse flow and pressure into the superior vena cava. Other problems associated with severe TR include liver congestion due to reverse pressure to the inferior vena cava and the liver veins, and fatigue and general malaise because of decreased pumping of blood through the heart (that is, decreased cardiac output), that may progress to cardiac cirrhosis and liver dysfunction with prolonged hepatic congestion. Furthermore, high venous pressure may contribute to renal dysfunction and other symptoms of abdominal bloating. All these findings are dependent on the severity of tricuspid regurgitation and pulmonary hypertension. Often the end effect is right heart failure.

Tricuspid regurgitation can be alleviated or eliminated by surgical means, either by replacement of the total valve apparatus with an artificially fabricated replacement tricuspid heart valve, or by constriction of the valve ring with means of an annular remodeling ring (annuloplasty ring). The tricuspid valve repair is not always 100% effective in eliminating the TR, as it has been found in some instances that patients (up to about 15%) who have undergone tricuspid valve annuloplasty may leave the hospital with moderate to severe TR and the tricuspid dysfunction rate may steadily increase to about 30-50%. If surgery is impossible to perform, i.e., if the patient is deemed inoperable or operable only at a too high surgical risk, an alternative possibility is to treat the patient with a stented valvular device and percutaneous means of device delivery for protecting the upper and lower body from high venous pressures.

U.S. Pat. No. 6,503,272 issued on Jan. 7, 2003, entire contents of which are incorporated herein by reference, discloses an artificial venous valve which incorporates a stent having one or more of the elements comprising its frame deformed inwardly towards its center and a biocompatible fabric attached to the one or more elements utilized to replace or supplement incompetent or damaged venous valves.

U.S. Pat. No. 5,855,601 issued on Jan. 5, 1999, entire contents of which are incorporated herein by reference, discloses an artificial venous valve comprising a tubular valve segment containing venous valve means and at least one self-expanding, cylindrical stent member having a plurality of barbs extending from the outer surface of the stent member to engage the natural tissue of the site to hold the valve in place after implantation.

U.S. Pat. No. 6,299,637 issued on Oct. 9, 2001, entire contents of which are incorporated herein by reference, discloses a self expandable prosthetic venous valve comprising a tubular wire support, expandable from a first reduced diameter to a second enlarged diameter, and at least one leaflet pivotably positioned in the flow path for permitting flow in a forward direction and resisting flow in a reverse direction.

U.S. Pat. No. 5,824,061 issued on Oct. 20, 1998, entire contents of which are incorporated herein by reference, discloses an endovascular venous valve prosthesis comprising an endovascular stent assembly including a stent having a generally cylindrical body with a hollow bore extending longitudinally therethrough and first and second support struts formed on opposite sides of the outflow end of the cylindrical body and extending generally longitudinally therefrom; and a preserved segment of vein having an outer wall and a venous valve positioned therein, the valve having two leaflets extending generally longitudinally within the segment of vein with lateral edges adjacent the outer wall.

U.S. Pat. No. 5,607,465 issued on Mar. 4, 1997, entire contents of which are incorporated herein by reference, discloses a valve for use in a blood vessel having a bent flexible wire mesh with elasticity and plasticity so as to be collapsible and implantable remotely at a desired site and a monocusp sail-like valving element mounted onto it.

U.S. Pat. No. 5,997,573 issued on Dec. 7, 1999, entire contents of which are incorporated herein by reference, discloses a dilation restrictor apparatus for limiting the extent to which a blood vessel may dilate adjacent to a point whereat a cut end of the blood vessel has been anastomosed to a venous valve implant, the dilation restrictor apparatus comprising an elongate tubular body having a hollow bore containing a plurality of apertures formed therein to permit passage of fluid therethrough.

U.S. Pat. No. 6,383,193 issued on May 7, 2002, entire contents of which are incorporated herein by reference, discloses a delivery system for the percutaneous insertion of a self-expanding vena cava filter device being formed with a length along a longitudinal filter axis, the system comprising constraining the filter in a compact condition within an elongated, radially flexible and axially stiff tubular member and a displacement member attached to the tubular member for displacing the filter from the segment thereby to deploy the filter.

None of the above-referenced prior art discloses means for protecting the upper body and lower body of a patient from spiked or elevated venous pressure resulting from cardiac tricuspid valve regurgitation.

Therefore, it is one preferred object to provide a method of protecting an upper body and a lower body of a patient from high venous pressures comprising implanting an elongate valve stent having a first valved stent member placed at a superior vena cava and a second valved stent member placed at an inferior vena cava, wherein both stent members are collapsibly expandable and wherein the first and second valved stent members are configured to permit blood flow towards the right atrium of the patient and prevent blood flow in an opposite direction.

SUMMARY OF THE INVENTION

In general, it is one object of the present invention to provide stented valve bioprostheses and methods for reduction of pressure effects of cardiac tricuspid valve regurgitation.

In one aspect of the invention, it is provided an elongate valve stent comprising a first end, a middle section, and an opposite second end that is connected to the first end with a plurality of spaced apart elongate connecting members; a first stent member disposed at and secured to the first end, the first stent member comprising a first support structure and a first tissue valve; and a second stent member disposed at and secured to the second end, the second stent member comprising a second support structure and a second tissue valve. In a preferred embodiment, each tissue valve is configured to permit fluid flow towards the middle section and prevent fluid flow in an opposite direction.

In some aspect of the invention, it is provided a method of protecting an upper and a lower body of a patient from high venous pressures comprising providing an elongate valve stent, wherein the stent comprises a first stent member with a first tissue valve secured to a first support structure being disposed at a first end of the stent and a second stent member with a second tissue valve secured to a second support structure being disposed at an opposite second end of the stent, wherein both support structures are collapsibly expandable, the second end being connected to the first end with at least one elongate connecting member; passing the elongate valve stent through a blood vessel with the first and second support structures in a collapsed position; and securing the first support structure to the inferior vena cava and the second support structure to the superior vena cava with both support structures in an expanded shape.

In a preferred aspect, at least a portion of the elongate valve stent is coated with a therapeutic agent, wherein the therapeutic agent is selected from a group consisting of anticoagulants, antithrombogenic agents, anti-proliferative agents, anti-inflammatory agents, antibiotics, stem cells, growth factors, angiogenesis agents, anti-angiogenesis agents, and statins.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

The preferred embodiments of the present invention described below relate particularly to venous valve bioprostheses and methods for reduction of pressure effects of cardiac tricuspid valve regurgitation. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

A stented valve or valved stent is a device to be placed inside a channel of the body that allows fluid flow in one direction and prevents fluid flow in an opposite direction. In a normal person, the superior vena cava functions to bring blood to the heart from the head and the inferior vena cava functions to bring blood to the heart from the liver and other parts of the body (kidneys, gut, legs) that are located below the heart.

In instances where the tricuspid valve (54 in FIG. 7) is unable to close properly, the pumping pressure of the ventricle 53 can be transmitted in reverse to the atrium 52 and subsequently to the vena cavae 55, 56. This pressure can have deleterious effects on the work of the heart and circulatory system. It is one aspect of the invention to provide a device and methods enabling reduction or total nullification of the effects of elevated pressure on the channels of venous return to the heart.

Figure 1:
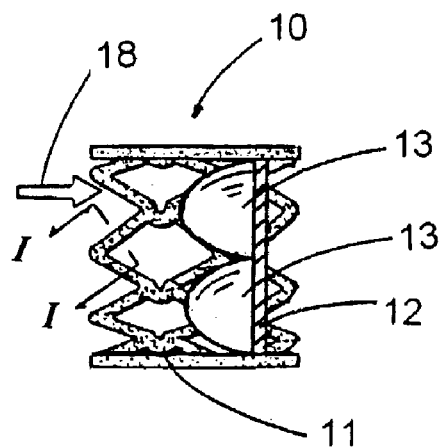
FIG. 1 is a front view of a stented valve according to the principles of the present invention.
Figure 2:
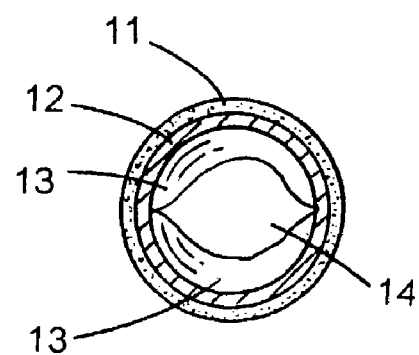
FIG. 2 is a side view of the stented valve of FIG. 1.

FIG. 1 shows a front view of a stented valve while FIG. 2 shows its side view according to the principles of the present invention. The stented valve 10 comprises a tissue valve secured to a support structure 11, wherein the support structure is collapsibly expandable. The tissue valve comprises at least one leaflet 13 securely attached to an annular base 12. The tissue valve is configured to permit fluid flow in a first direction (as shown by the arrow 18) and prevent fluid flow in an opposite direction. When the fluid flows in the first direction, the leaflet 13 is open having a flow-through opening 14.

In one embodiment, the support structure 11 of the stented valve 10 is self-expandable out of a delivery sheath. In operations, the stent is compressed radially to be held within the lumen of the delivery apparatus, sheath, catheter, applicator, or cannula. Upon delivery out of the apparatus, the stent self-expands to its pre-compressed state. The stent is typically made of a material selected from a group consisting of stainless steel, Nitinol, plastics or the like. In another embodiment, the stent 11 of the stented valve 10 is expandable by an inflatable balloon, which is well known to an ordinary artisan who is skilled in the art.

In still another embodiment, the support structure 11 is made of a shape-memory material having a first shape transition temperature of between about 30° C. and 45° C. and a second shape transition temperature of between about 5° C. and −10° C. In operations, the stent is collapsibly deformed to a small diameter and held at about or below 5° C., preferably between about 5° C. and −10° C. The deformed stent is then inserted within a delivery apparatus. During delivery, the stent is maintained at below the second shape transition temperature by flushing or contacting with super-cooled saline. At a desired location, the stent is pushed out of the sheath. Upon reaching the first shape transition temperature, the stent expands to lock itself in position.

The use of shape memory alloys or intermetallics and, specifically, Nitinol in the construction of medical devices is well known. U.S. Pat. No. 6,451,025 issued on Sep. 17, 2002, entire contents of which are incorporated herein by reference, discloses hysteresis behavior of Nitinol to generate shape change or force at or around constant body temperature by forming the device to the final shape desired, straining the device in a direction which tends to facilitate placement into the body, restraining the device in this strained shape during insertion into or placement near the body, then releasing all or part of the device such that it returns or tends to return to the desired shape with temperature activation.

Figure 7:
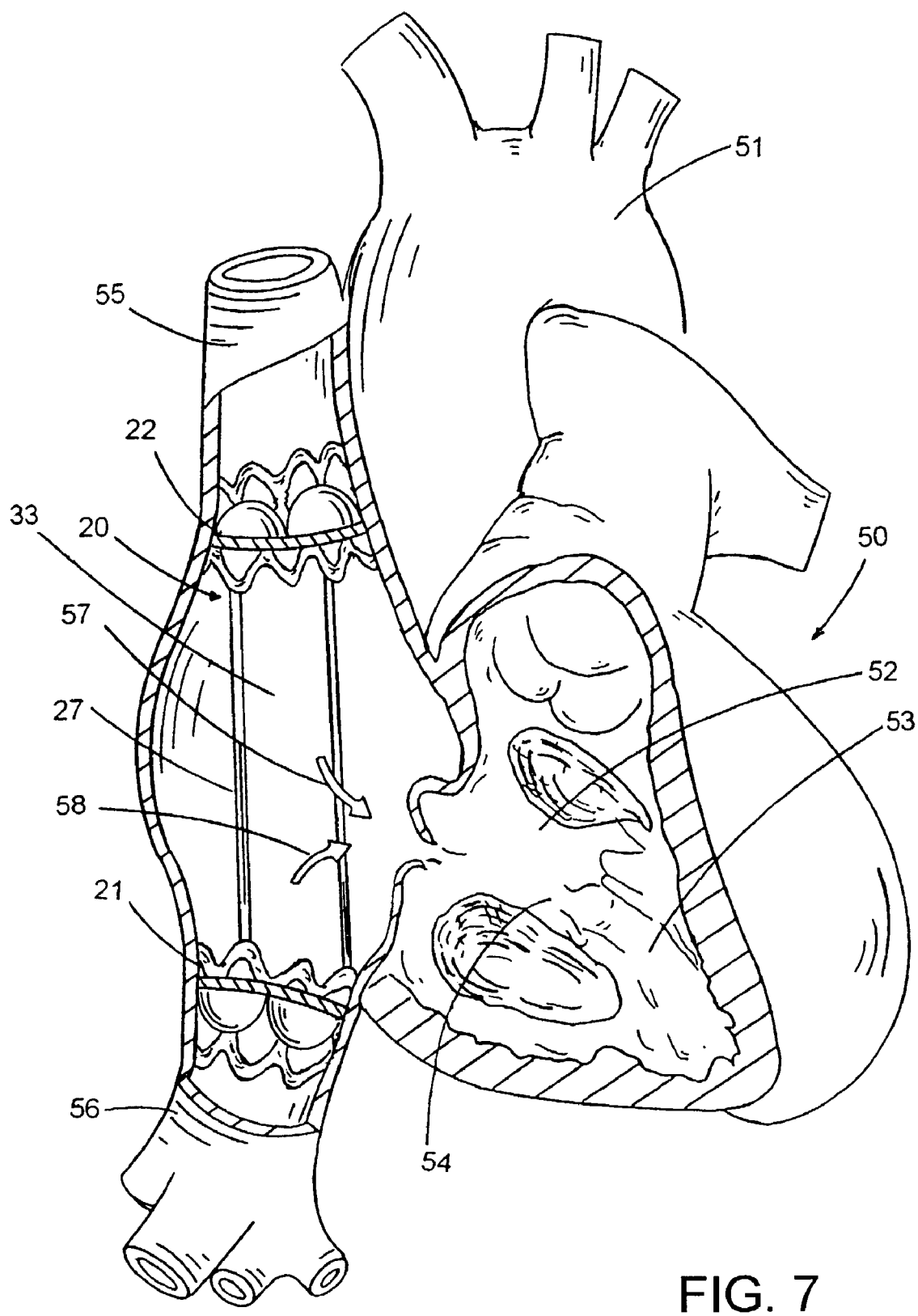
FIG. 7 is a preferred procedure of implanting an elongate valve stent having two stent members, wherein a first stent member with a supported valve is placed at the superior vena cava and another stent member with a supported valve is placed at the inferior vena cava configured to permit blood flow towards the right atrium of a patient.

FIG. 7 shows a preferred embodiment of procedures of protecting an upper body and a lower body of a patient from high venous pressures, the method comprising implanting an elongate valve stent 20 having a first valved stent member 22 suitably placed at a superior vena cava 55 location and a second valved stent member suitably placed at an inferior vena cava 56 location, wherein the first stent member 22 and the second stent member 21 are configured to permit blood flow (as indicated by arrows 57, 58) towards a right atrium 52 of the heart 50 and prevent blood flow in an opposite direction. In a normal patient, the oxygenated blood is pumped from the heart 50 through aorta 51 to the body.

In one aspect, the first stent member 22 of the elongate valve stent 20 is delivered to the superior vena cava 55 endoluminally from a femoral vein and simultaneously delivering the second stent member 21 of the valve stent 20 to the inferior vena cava 56. In another aspect, the second stent member 21 of the elongate valve stent 20 is delivered first from a subclavian vein or jugular vein simultaneously delivering the first stent member 22 of the valve stent 20 to the superior vena cava 56.

The step of delivering the elongate valve stent endoluminally is through an incision at a blood vessel selected from a group consisting of a jugular vein, a femoral vein, and a subclavian vein. The stent member is collapsibly expanded when the member is placed at an appropriate site. In a further aspect, the stent members 21, 22 further comprise means for anchoring the stent onto surrounding tissue of either the superior vena cava or the inferior vena cava, for example hooks, barbs, needles, protrusion, or the like that is well known to one who is skilled in the art.

In an alternate embodiment, the venous valve to be placed at either the superior vena cava or the inferior vena cava is a stentless valve. In still another embodiment, the venous valves are to be implanted by an open chest procedure at the superior vena cava and the inferior vena cava, wherein the valves can be either a stented valve or a stentless valve.

In a preferred embodiment, the valved stent member 22 would deploy in the superior vena cava 55 just above the right atrial junction but below the azygos vein, whereas the valved stent member 21 would deploy in the inferior vena cava 56 just below the right atrium 52 but above the hepatic veins. In effect, the physiologic changes from the therapy disclosed herein would be to protect the upper and lower body from high or elevated venous pressures. Patients with severe tricuspid regurgitation are troubled by ascites, peripheral edema frequently with stasis changes in the legs, hepatic congestion, which may progress to cardiac cirrhosis and liver dysfunction with prolonged hepatic congestion. Furthermore, high venous pressure may contribute to renal dysfunction and other symptoms of abdominal bloating. The neck vein and upper body congestion is sometimes quite visible in patients including the pulsatile neck veins. By placing the stented valves, it should protect the patient from ascites, hepatic congestion, edema and the eventual development of cardiac cirrhosis.

Figure 3:
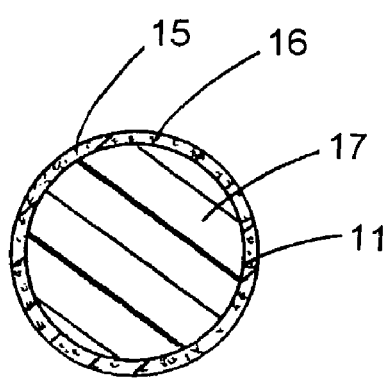
FIG. 3 is a cross-sectional view of the stent strut, section I-I, of the stented valve in FIG. 1.

To enhance the biocompatibility of the device or improved therapy to the surrounding tissue, it is provided that at least a portion of the stent member 21, 22 of the elongate valve stent 20, 40 is coated with a therapeutic agent, wherein the therapeutic agent is selected from a group consisting of anticoagulants, antithrombogenic agents, anti-proliferative agents, anti-inflammatory agents, antibiotics, stem cells, growth factors, angiogenesis agents, anti-angiogenesis agents, and statins. The therapeutic agent is to slowly release to the tissue at an effective amount over time. For illustration purposes, FIG. 3 shows a cross-sectional view of the stent strut 17 of the stent 11, section I-I, of the stented valve 10 in FIG. 1, wherein a polymer layer 16 is coated onto the periphery surface of the stent strut 17 and the polymer layer 16 is loaded with the desired therapeutic agent 15 for slow release at an effective amount over time to the surrounding tissue.

Many medical materials used in the treatment of cardiovascular diseases are required to possess biocompatible and hemo-compatible properties without antigenicity. One method to treat tissue so as to render the tissue more suitable as a biomaterial is a process called chemical treatment. Several chemical treatment agent and methods have been disclosed. Among them, aldehydes (glutaraldehyde, formaldehyde, dialdehyde starch and the like), epoxy compounds, genipin, and their analog or derivatives thereof are all applicable in treating a tissue. Chemical treatment conditions and procedures to render the tissue suitable as a biomaterial depend on the property of each tissue and intended medical applications, wherein the conditions/procedures are well documented in published literature and well known to one who is skilled in the art.

The tissue valve of the stented valve 10 has at least one valve leaflet 13. Sometimes, the tissue valve may have two, three or more leaflets. In some aspect of the present invention, the leaflet 13 is made from a pericardium, the pericardium being selected from a group consisting of a bovine pericardium, an equine pericardium, a porcine pericardium, an ovine pericardium and the like. Further, the tissue valve is chemically treated with a chemical treating agent selected from a group consisting of glutaraldehyde, formaldehyde, dialdehyde starch, epoxy compounds, genipin, and mixture thereof. In one embodiment, the tissue valve is a venous valve selected or procured from a group consisting of a bovine jugular vein, an equine jugular vein, a porcine jugular vein, and an ovine jugular vein. In another embodiment, the tissue valve is a porcine valve.

U.S. Pat. No. 4,806,595 issued on Feb. 21, 1989, entire contents of which are incorporated herein by reference, discloses a novel method for preparing medical materials by using epoxy compounds as chemical treatment agent for tissue, wherein the "epoxy compounds" include glycol diglycidyl ether, polyol polyglycidyl ether, dicarboxylic acid diglycidylester, the analog, and derivatives thereof.

Figure 4:
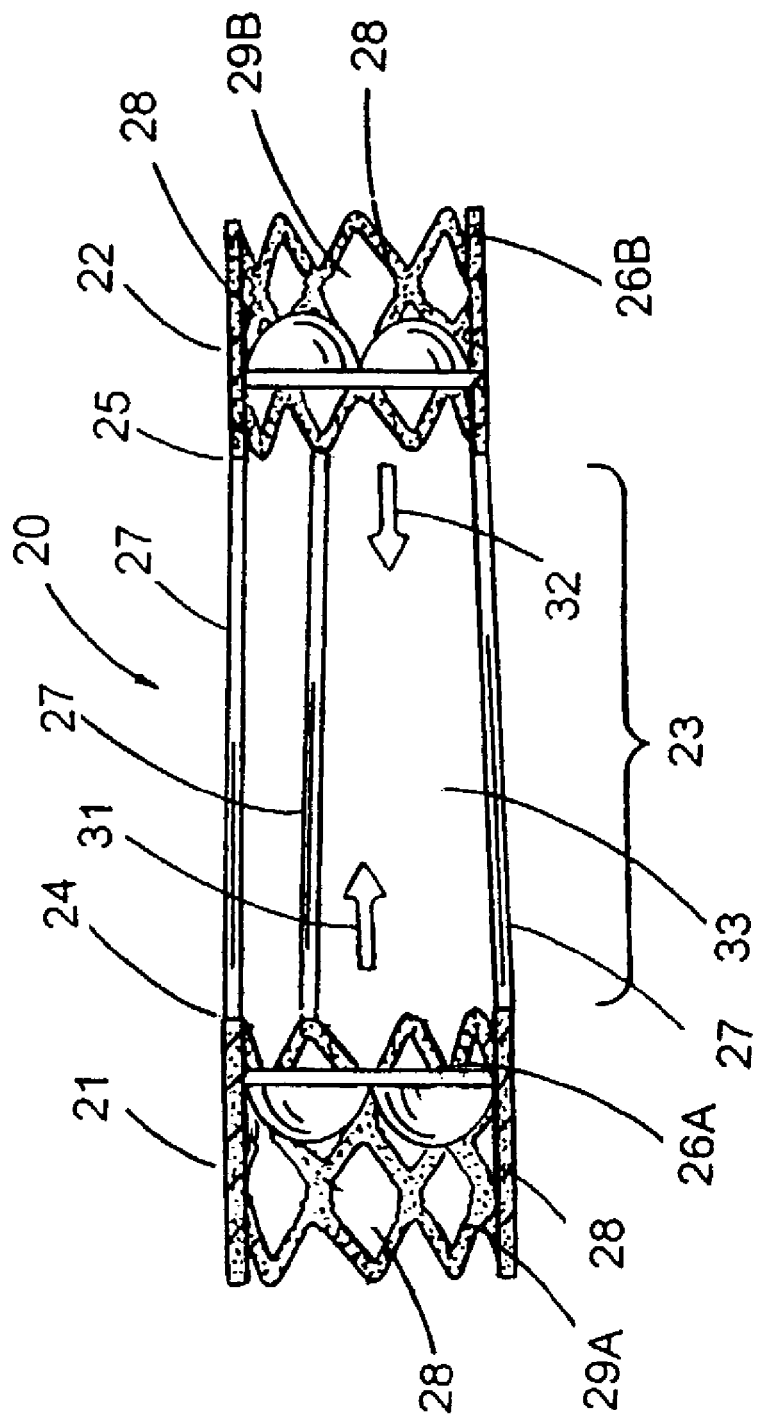
FIG. 4 is a preferred embodiment of an elongate valve stent in accordance with the principles of the present invention.

FIG. 4 shows a preferred embodiment of an elongate valve stent in accordance with the principles of the present invention. In some aspect, it is provided an elongate valve stent 20 comprising a first end 24, a middle section 23, and an opposite second end 25 that is connected to the first end 24 with a plurality of spaced apart elongate connecting members 27. The elongate valve stent 20 further comprises a first stent member 21 disposed at and secured to the first end 24, the first stent member 21 comprising a first support structure 26A with amounted first tissue valve 29A and a second stent member 22 disposed at and secured to the second end 25, the second stent member 22 comprising a second support structure 26B with a mounted second tissue valve 29B. In one preferred embodiment, the first tissue valve 29A having at least one valve leaflet 28 is configured to permit fluid flow towards (shown by an arrow 31) the middle section 23 and prevent fluid flow in an opposite direction. Similarly, the second tissue valve 29B having at least one valve leaflet 28 is configured to permit fluid flow towards (shown by an arrow 32) the middle section 23 and prevent fluid flow in an opposite direction.

In one aspect, the space 33 between any two spaced apart elongate connecting members 27 allows fluid to freely flow out of the construct of the elongate valve stent 20 at about the middle section 23. In another aspect, the first stent member 21 is secured to the second stent member 22 by only one elongate connecting member. Depending on the design and applications, the at least one elongate connecting member 27 may suitably be in any appropriate size, shape, length or configuration.

Figure 5:
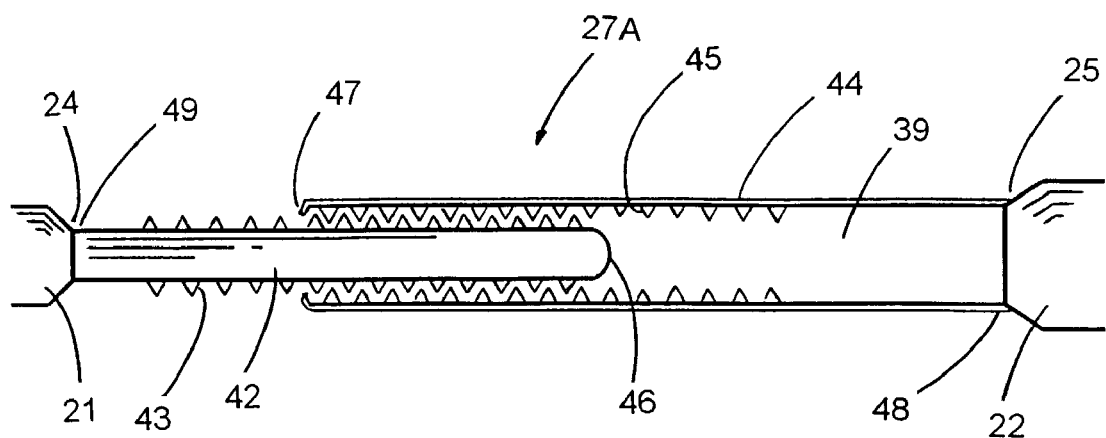
FIG. 5 is a detailed embodiment of an elongate connecting member with adjustable length.

In some aspect, the at least one elongate connecting member is adjustable in length so as to suitably position the first stent member 21 at the inferior vena cava and the second stent member 22 at the superior vena cava. FIG. 5 shows a detailed embodiment of an elongate connecting member with adjustable length. Other mechanism for adjusting the length of the connecting member 27A is also within the scope of the present invention. The adjustable connecting member 27A is to connect the first end 24 of the first stent member 21 to the second end 25 of the second stent member 22. In one aspect, the adjustable connecting member 27A comprises a pair of the matching rod element 42 and a tubing element 44, wherein the tubing element 44 is slidably riding over the rod element 42 with traction or appropriate frictional force for holding. The rod element 42 comprises a rod end 46 and a rod base 49 securely connected to the first end 24 while the tubing element 44 comprises a tubing end 47 and a tubing base 48 securely connected to the second end 25. After sliding the rod end 46 into the lumen 39 of the tubing element 44, the length of the connecting member 27A becomes adjustable to fit the needs. Any conventional means for adjusting the length of the connecting member 27A is also herein applicable.

To provide proper traction, in one embodiment, the rod element 42 comprises a plurality of first ribs or protrusions 43 suitably flexible to match and temporarily retain the opposite plurality of second ribs or protrusions 45. The first protrusions 43 and the second protrusions 45 are sized and configured to provide adequate traction between the rod element and the tubing element, but allow the tubing element to slide over the rod element by an operator so as to adjust the length at will. The elongate valve stent with adjustable length between the first stent member 21 and the second stent member 22 will allow easier sizing and reduce the number of stent/valve sizes that need to be developed. For example, the operator chooses a 22 mm first stent member 21 to be implanted at the inferior vena cava based on an echo imaging. He can then position an 18 mm second member 22 by sliding the second stent member 22 to an appropriate position at the superior vena cava based on an echo data.

Figure 6:
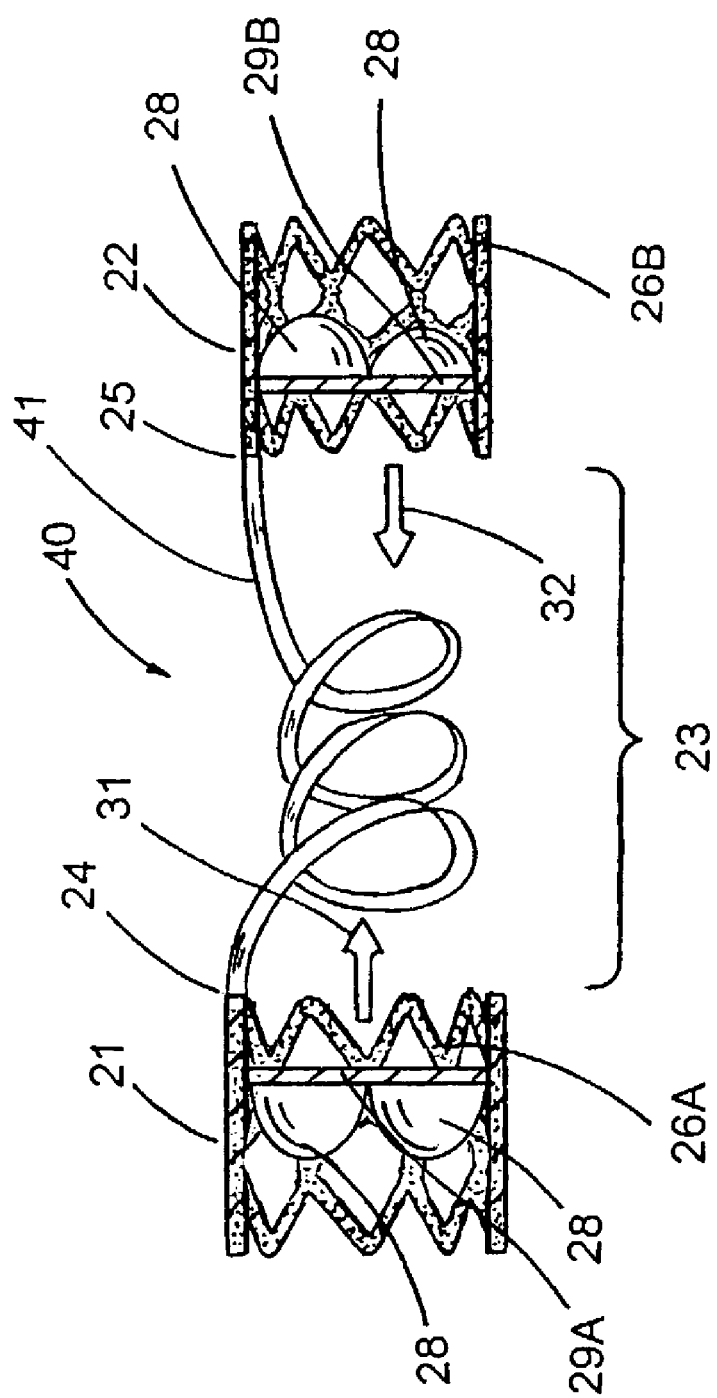
FIG. 6 is another preferred embodiment of an elongate valve stent in accordance with the principles of the present invention.

FIG. 6 shows another preferred embodiment of an elongate valve stent 40 in accordance with the principles of the present invention. In some aspect, it is provided an elongate valve stent 40 comprising a first end 24, a middle section 23, and an opposite second end 25 that is connected to the first end 24 with at least one connecting member 41. The connecting member 41 is sized and configured to provide radial flexibility and longitudinal stiffness for the elongate valve stent 40 enabling percutaneous delivery by a stent delivery apparatus to a desired implantation place, wherein the connecting member 41 may be a spiral wire in the shape of a coil, a helix, a zigzag, or other irregular configuration. The length of the connecting member 41 may be adjustable.

Further, the connecting member 41 may have a lower circumferential profile enabling the connecting member portion being held within the lumen of the stent delivery apparatus without compression or collapsing. The elongate valve stent 40 further comprises two stent members 21 and 22, each disposed at the first and second end 24, 25 respectively, wherein each stent member 21, 22 comprises a support structure 26A, 26B and a tissue valve 29A, 29B with at least one valve leaflet 28. The tissue valve 29A or 29B is configured to permit fluid flow towards (shown by arrows 31 and 32) the middle section 23 and prevent fluid flow in an opposite direction.

The support structures 29A, 29B of the elongate valve stent 20 or 40 are configured collapsibly expandable from a first collapsed position to a second expanded position, wherein the stent is delivered through a blood vessel with the support structures in the collapsed position and the stent is secured to a desired valve location at the superior and inferior vena cava with the support structures in the expanded shape. In an alternate embodiment, the elongate valve stent 20, 40 can be implanted by an open chest procedure at the superior vena cava and the inferior vena cava.

In one embodiment, the circumference of the first support structure 29A at the expanded position is equal to the circumference of the second support structure 29B at the expanded position. In another embodiment, the circumference of the first support structure 29A at the expanded position is larger than the circumference of the second support structure 29B at the expanded position. The support structure 29A, 29B may be self-expandable, expandable by an inflatable balloon, or by other expanding means. Further, the support structure of the stent member 21, 22 is made of a shape-memory material having a first shape transition temperature of between about 30° C. and 45° C. and a second shape transition temperature of between about 5° C. and −10° C. In operations, the support structure is collapsibly deformed to a small diameter and held at about or below 5° C., preferably between about 5° C. and −10° C. The deformed support structure is then inserted within a delivery apparatus. During delivery, the support structure 26A, 26B with its mounted tissue valve 29A, 29B is maintained at below the second shape transition temperature by flushing or contacting with super-cooled saline. At a desired location, the elongate valve stent 20, 40 is pushed out of the sheath. Upon reaching the first shape transition temperature, each of the support structures 29A, 29B expands to lock itself in position.

The support structure 11 or support structures 29A, 29B are made of shape memory Nitinol with at least one shape transition temperature. In one embodiment, the stent or the support structures are sized and configured to be reversibly collapsed by lowering the Nitinol temperature below its second shape transition temperature (about 5° C. and −10° C.) enabling removing the stent or the support structures from a patient percutaneously when needed. This is usually carried out by a retrieval apparatus by grasping the radially deformed device endoluminally.

FIG. 7 shows a process or procedure of implanting an elongate valve stent 20 having two stent members 21, 22, wherein the stent member 22 is placed at a superior vena cava 55 and another stent member 21 is placed at an inferior vena cava 56 configured to permit blood flow in a direction shown by the arrows 57, 58 towards the right atrium, wherein each stent member 21, 22 comprises a support structure with a mounted tissue valve having at least one valve leaflet.

In some aspect of the invention, it is provided a method of protecting an upper body and a lower body of a patient from high venous pressures comprising implanting an elongate valve stent having a first valved stent 22 at a superior vena cava and a second valved stent 21 at an inferior vena cava, wherein the first and second valved stents are configured to permit blood flow towards a right atrium of the patient and prevent blood flow in an opposite direction. The first valves or the second valved stent may comprise a stented valve.

In some preferred aspect of the invention, it is provided a method of protecting an upper and a lower body of a patient from high venous pressures comprising: (a) providing an elongate valve stent 20 or 40, wherein the stent comprises a first stent member 21 with a first tissue valve 29A secured to a first support structure 26A being disposed at a first end 24 of the stent and a second stent member 22 with a second tissue valve 29B secured to a second support structure 26B being disposed at an opposite second end 25 of the stent, wherein both support structures are configured collapsibly expandable, the second end being connected to the first end with at least one elongate connecting member; (b) passing the elongate valve stent 20, 40 through a blood vessel with the first support structure 26A and the second support structure 26B in a collapsed position; and (c) securing the first support structure of the first stent member 21 to an inferior vena cava and the second support structure of the second stent member 22 to a superior vena cava with both support structures in an expanded shape.

Figure 8:
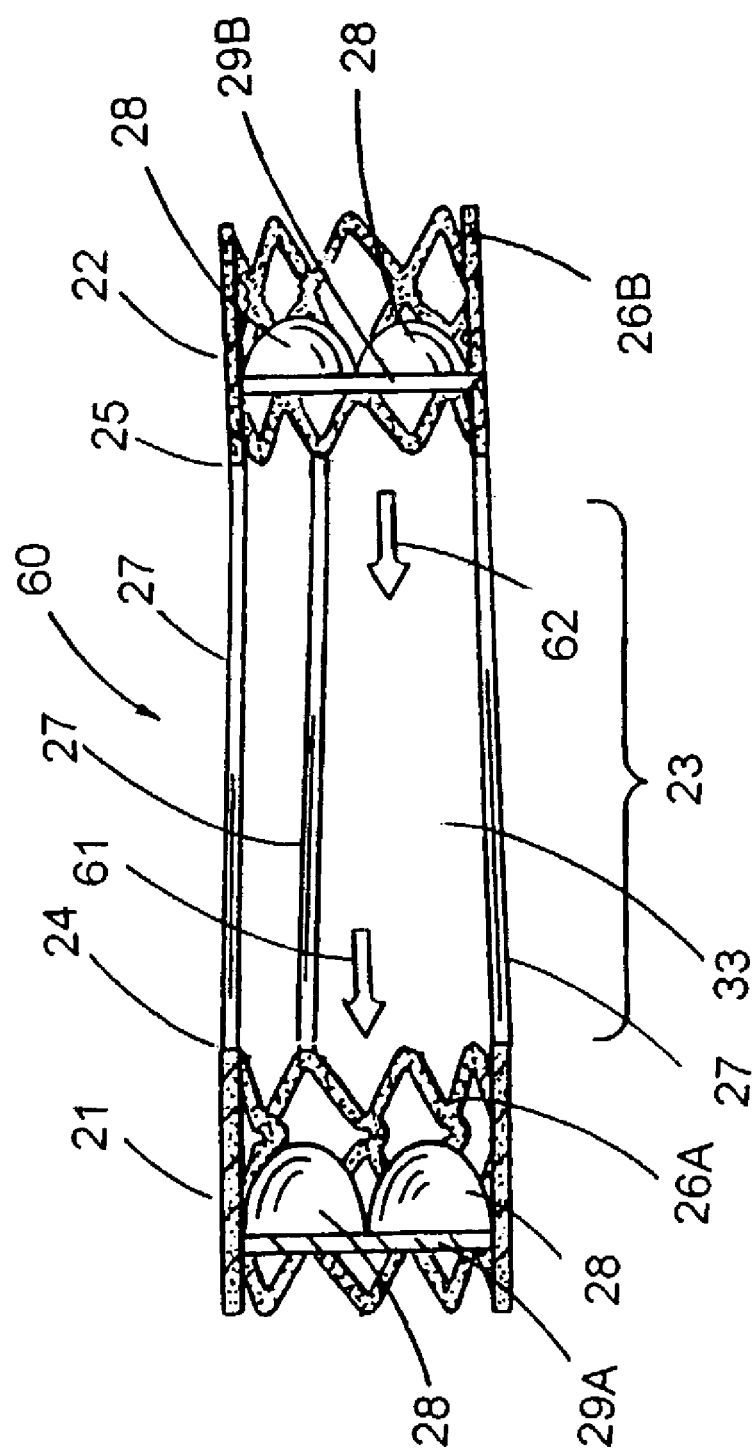
FIG. 8 is a further preferred embodiment of an elongate valve stent configured for venous valve application in accordance with the principles of the present invention.

FIG. 8 shows a further preferred embodiment of an elongate valve stent 60 configured for general venous valve applications in accordance with the principles of the present invention. An elongate valve stent 60 comprises a first end 24, a middle section 23, and an opposite second end 25 that is connected to the first end 24 with at least one elongate connecting member 27 which may comprise an adjustable length. The stent 60 further comprises a first stent member 21 disposed at and secured to the first end 24, the first stent member 21 comprising a first support structure 26A and a first tissue valve 29A and a second stent member 22 disposed at and secured to the second end 25, the second stent member 22 comprising a second support structure 26B and a second tissue valve 29B. In some aspect, the second tissue valve 29B of the elongate valve stent 60 is configured to permit fluid flow towards the middle section (shown by an arrow 62) and the first tissue valve 29A is configured to permit fluid flow from the middle section 23 towards the first end 24 and out of the elongate valve stent 60 (shown by an arrow 61). One specific advantage of the double-valved elongate valve stent 60 is to provide double assurance for eliminating the regurgitation potential in an implanted valve, such as a prosthetic venous valve or cardiac valve.

Although preferred embodiments of the invention have been described in detail, certain variations and modifications will be apparent to those skilled in the art, including embodiments that do not provide all of the features and benefits described herein. Accordingly, the scope of the present invention is not to be limited by the illustrations or the foregoing descriptions thereof, but rather solely by reference to the appended claims.

What is claimed is:

1. An elongate valve stent comprising:
   a first stent member comprising a first support structure including a plurality of serpentine bands, wherein adjacent serpentine bands are connected by at least one connector strut and a first tissue valve disposed thereon, said first tissue valve including at least two leaflets structured to open and close permitting the flow of blood therethrough in the open position;
   a second stent member distinct and separated from said first stent member by a predetermined distance, said second stent member comprising a second support structure including a plurality of serpentine bands, wherein adjacent serpentine bands are connected by at least one connector strut and a second tissue valve disposed thereon, said second tissue valve including at least two leaflets structured to open and close permitting the flow of blood therethrough in the open position; and
   at least two elongate connecting members extending between and connecting at least one serpentine band of the first stent member to at least one serpentine band of the second stent member.

2. The elongate valve stent of claim 1, wherein said first tissue valve is configured to permit fluid flow towards the middle section and prevent fluid flow in an opposite direction.

3. The elongate valve stent of claim 1, wherein said second tissue valve is configured to permit fluid flow towards the middle section and prevent fluid flow in an opposite direction.

4. The elongate valve stent of claim 1, wherein said first tissue valve is configured to permit fluid flow towards the middle section and the second tissue valve is configured to permit fluid flow from the middle section towards the second end.

5. The elongate valve stent of claim 1, wherein the first and second support structures are collapsibly expandable from a first collapsed position to a second expanded position.

6. The elongate valve stent of claim 5, wherein a circumference of the first support structure at the expanded position is equal to a circumference of the second support structure at the expanded position.

7. The elongate valve stent of claim 5, wherein a circumference of the first support structure at the expanded position is larger than a circumference of the second support structure at the expanded position.

8. The elongate valve stent of claim 1, wherein both support structures of said stent are self-expandable.

9. The elongate valve stent of claim 1, wherein the first or second support structure of said stent is expandable by an inflatable balloon.

10. The elongate valve stent of claim 1, wherein the first or second support structure of said stent is made of a shape-memory material having a first shape transition temperature of between about 30.degree. C. and 45.degree. C. and a second shape transition temperature of about 5.degree. C. and −10.degree. C., said support structure being collapsibly deformed to below the second shape transition temperature during delivery and expanded after delivery in place upon reaching the first shape transition temperature.

11. The elongate valve stent of claim 1, wherein said at least two leaflets are made from a pericardium.

12. The elongate valve stent of claim 11, wherein the pericardium is selected from a group consisting of a bovine pericardium, an equine pericardium, a porcine pericardium, and an ovine pericardium.

13. The elongate valve stent of claim 1, wherein said at least two leaflets are chemically treated by a chemical treating agent selected from a group consisting of glutaraldehyde, formaldehyde, dialdehyde starch, epoxy compounds, genipin, and mixture thereof.

14. The elongate valve stent of claim 1, wherein said first or second tissue valve is a venous valve procured from a group consisting of a bovine jugular vein, an equine jugular vein, a porcine jugular vein, and an ovine jugular vein.

15. The elongate valve stent of claim 1, wherein said first or second tissue valve is a porcine valve.

16. The elongate valve stent of claim 1, wherein the elongate connecting members are essentially parallel to each other or in a spiral shape.

17. The elongate valve stent of claim 1, wherein said first or second support structure is made of a material selected from a group consisting of stainless steel, Nitinol, and plastics.

18. The elongate valve stent of claim 1, wherein said first or second support structure is coated with a therapeutic agent.

19. The elongate valve stent of claim 18, wherein said therapeutic agent is selected from a group consisting of anti-coagulants, antithrombogenic agents, anti-proliferative agents, anti-inflammatory agents, antibiotics, stem cells, growth factors, angiogenesis agents, anti-angiogenesis agents, and statins.

20. The elongate valve stent of claim 1, wherein said first or second support structure further comprises means for anchoring said first or second support structure onto surrounding tissue of either the superior vena cava or the inferior vena cava.

21. The elongate valve stent of claim 1, wherein the at least one elongate connecting member comprises a length that is adjustable.

22. The elongate valve stent of claim 1 wherein said first stent member is configured to be implanted in a superior vena cava.

23. The elongate valve stent of claim 1 wherein said second stent member is configured to be implanted in an inferior vena cava.

24. The elongate valve stent of claim 1 wherein said first stent member is configured to be implanted in a superior vena cava and said second stent member is configured to be implanted in an inferior vena cava.

25. A elongate valve stent for protecting an upper body and a lower body of a patient from high venous pressures comprising:
a first stent member comprising a first support structure including a plurality of serpentine bands, wherein adjacent serpentine bands are connected by at least one connector strut and a first tissue valve disposed thereon, said first tissue valve structured to be implanted in a superior vena cava and including at least two leaflets structured to open and close permitting the flow of blood therethrough in the open position;
a second stent member distinct and separate from said first stent member, said second stent member comprising a second support structure including a plurality of serpentine bands, wherein adjacent serpentine bands are connected by at least one connector strut and a second tissue valve disposed thereon, said second tissue valve structured to be implanted in an inferior vena cava and including at least two leaflets structured to open and close permitting the flow of blood therethrough in the open position; and
at least one elongate connecting member extending between and connecting at least one serpentine band of the first stent member to at least one serpentine band of the second stent member
wherein said first and second valves are configured to permit blood flow towards a right atrium and prevent blood flow in an opposite direction.

26. An elongate valve stent comprising:
a first stent member comprising a first support structure including a plurality of serpentine bands, wherein adjacent serpentine bands are connected by at least one connector strut and a first tissue valve disposed thereon;
a second stent member separate and distinct from said first stent member, said second stent member comprising a second support structure including a plurality of serpentine bands, wherein adjacent serpentine bands are connected by at least one connector strut and a second tissue valve disposed thereon; and
at least one elongate connecting member sized and configured to provide radial flexibility and longitudinal stiffness, said elongate connecting member extending between and connecting at least one serpentine band of the first stent member to at least one serpentine band of the second stent member.

* * * * *